United States Patent
Doi et al.

(10) Patent No.: US 7,615,063 B2
(45) Date of Patent: Nov. 10, 2009

(54) NERVE REGENERATION-INDUCING TUBE COMPRISING

(75) Inventors: Nobutoshi Doi, Osaka (JP); Hideaki Murahashi, Osaka (JP); Kenichiro Hata, Kariya (JP)

(73) Assignees: Nipro Corporation, Osaka (JP); Minoru Ueda, Nisshin-nishi (JP)

( * ) Notice: Subject to any disclaimer, the term of this patent is extended or adjusted under 35 U.S.C. 154(b) by 776 days.

(21) Appl. No.: 10/540,621

(22) PCT Filed: Dec. 26, 2003

(86) PCT No.: PCT/JP03/17014

§ 371 (c)(1),
(2), (4) Date: Aug. 18, 2005

(87) PCT Pub. No.: WO2004/060208

PCT Pub. Date: Jul. 22, 2004

(65) Prior Publication Data

US 2006/0100647 A1    May 11, 2006

(30) Foreign Application Priority Data

Dec. 27, 2002   (JP)  .............................. 2002-379796

(51) Int. Cl.
*A61B 17/08* (2006.01)
(52) U.S. Cl. ...................... 606/152; 623/37.71
(58) Field of Classification Search ............... 606/152, 606/153, 154, 155, 156; 623/23.71, 23.75
See application file for complete search history.

(56) References Cited

U.S. PATENT DOCUMENTS

| | | | |
|---|---|---|---|
| 4,870,966 A | 10/1989 | Dellon et al. ........... | 128/334 R |
| 5,735,863 A | 4/1998 | Della Valle et al. ........ | 606/152 |
| 5,834,029 A * | 11/1998 | Bellamkonda et al. ...... | 424/570 |
| 6,090,117 A | 7/2000 | Shimizu .................... | 606/152 |
| 6,156,572 A | 12/2000 | Bellamkonda et al. ..... | 435/395 |
| 6,214,021 B1 * | 4/2001 | Hadlock et al. ............ | 606/152 |

(Continued)

FOREIGN PATENT DOCUMENTS

EP    0 945 145 A1    9/1999

(Continued)

OTHER PUBLICATIONS

Rosen, Joseph M. et al., "Fascicular Sutureless and Suture Repair of the Peripheral Nerves", *Orthopaedic Review*, vol. VIII, No. 4, 1979, pp. 85-92.

(Continued)

*Primary Examiner*—Anhtuan T Nguyen
*Assistant Examiner*—Tuan V Nguyen
(74) *Attorney, Agent, or Firm*—Kubovcik & Kubovcik

(57) ABSTRACT

The present invention provides a nerve regeneration-inducing tube in which nerve is inserted into a tubular structure and can be easily sutured and fixed without resort to any special instruments or operations, thereby allowing nerve cells to efficiently proliferate and grow in the correct direction. The nerve regeneration-inducing tube of the present invention includes: a tubular structure (A) made of a biodegradable material or a bioabsorbable material and provided inside with a matrix (B) having linear nerve-inducing channels and being made of a biodegradable material or a bioabsorbable material; and a definite space part provided at one end of the tubular structure (A).

13 Claims, 1 Drawing Sheet

U.S. PATENT DOCUMENTS

| | | | | |
|---|---|---|---|---|
| 6,953,482 B2 * | 10/2005 | Doi et al. | ................. | 623/23.71 |
| 2002/0161450 A1 * | 10/2002 | Doi et al. | ................. | 623/23.71 |

FOREIGN PATENT DOCUMENTS

| | | | |
|---|---|---|---|
| JP | 2002320630 | * | 11/2002 |
| JP | 5-237139 A | | 9/2005 |
| WO | 88/06871 A1 | | 9/1988 |
| WO | 02/47557 A1 | | 6/2002 |

OTHER PUBLICATIONS

Reid, R. L. et al.; "Biodegradable Cuff an Adjunct to Peripheral Nerve Repair: A Study in Dogs"; *The Hand*; vol. 10, No. 3, pp. 259-266; 1978.

Henderson, C. E. et al.; "Denervation Increases a Neurite-promoting Activity in Extracts of Skeletal Muscle"; *Nature*; vol. 302, pp. 609-611; 1983.

Mackinnon, S. E.; "Nerve Regeneration Through a Pseudosynovial Sheath in a Primate Model"; *Plastic and Reconstructive Surgery*; vol. 75, No. 6, pp. 833-839; 1985.

Nishimune, H. et al.; "Neurocrescin: A Novel Neurite-outgrowth Factor Secreted by Muscle After Denervation"; *NeuroReport*; vol. 8, pp. 3649-3654; 1997.

Ochi, M. et al.; "Promotion of Sciatic Nerve Regeneration in Rats by a New Neurotrophic Pyrimidine Derivative MS-430"; *Gen. Pharmac.*; vol. 26, No. 1, pp. 59-64; 1995.

Mackinnon, S. E. et al.; "Clinical Nerve Reconstruction with a Bioabsorbable Polyglycolic Acid Tube"; *Plastic and Reconstructive Surgery*; vol. 85, No. 3, pp. 419-424; 1990.

Aebischer, P. et al.; "Regeneration of Transected Sciatic Nerves Through Semi-Permeable Nerve Guidance Channels"; *Trans Am Soc Artif Intern Organs*; vol. XXXII, pp. 474-477; 1986.

McDonald, J. W.; "Transplanted Embryonic Stem Cells Survive, Differentiate and Promote Recovery in Injured Rat Spinal Cord"; *Nature Medicine*; vol. 5, No. 12, pp. 1410-1412; 1999.

Uyeda, A. et al.; "MDP77: A Novel Neurite-Outgrowth-Promoting Protein Predominantly Expressed in Chick Muscles"; *Biochemical and Biphysical Research Communications*; vol. 269, pp. 564-569; 2000.

Pu, L. et al.; "Effects of Nerve Growth Factor on Nerve Regeneration Through a Vein Graft Across a Gap"; *Plastic and Reconstructive Surgery*; vol. 104, No. 5, pp. 1379-1385; 1999.

Rosen, J. M. et al.; "Fascicular Tubulization: A Cellular Approach to Peripheral Nerve Repair"; *Annals of Plastic Surgery*; vol. 11, No. 5, pp. 397-411; 1983.

Terada, N. et al. "Bioartificial Nerve Grafts Based on Absorbable Guiding Filament Structures—Early Observations"; *Scand J Plast Reconstr Hand Surg*; vol. 31, pp. 1-6; 1997.

Henderson, C. E. et al.; "Neurite Outgrowth from Embryonic Chicken Spinal Neurons is Promoted by Media Conditioned by Muscle Cells"; *Proc. Natl. Acad. Sci.*; vol. 78, No. 4, pp. 2625-2629; 1981.

Gibson, K. L. et al.; "Comparison of Sciatic Nerve Regeneration Through Silicone Tubes and Nerve Allografts"; *Microsurgery*; vol. 10, pp. 126-129; 1989.

Molander, H. et al.; "Nerve Repair Using a Polyglactin Tube and Nerve Graft: An Experimental Study in the Rabbit"; *Biomaterials*; vol. 4, pp. 276-280; 1983.

Aebischer, P. et al.; "Blind-ended Semipermeable Guidance Channels Support Peripheral Nerve Regeneration in the Absence of a Distal Nerve Stump"; *Brain Research*; vol. 454, pp. 179-187; 1988.

Lundborg, G. et al.; "Regeneration of Peripheral Nerve Through a Preformed Tissue Space. Preliminary Observations on the Reorganization of Regenerating Nerve Fibres and Perineurium"; *Brain Research*; vol. 178, pp. 573-576; 1979.

Lundborg, G. et al.; "Bioartificial Nerve Grafts"; *Scand J Plast Reconstr Hand Surg*; vol. 30, pp. 105-110; 1996.

Nyilas, E. et al.; "Synthetic Bioresorbable Polymers: I. Polyester and Polyester Composite Guidance Channels for Peripheral Nerve Repair"; *9th Annual Meeting of the Society for Biomaterials*; 1983.

Lee, G. et al.; "Experimental Study of a Nerve Guide-Tube Made from Dehydrothermally Treated Gelatin Application to Repair of Gap in Rat Sciatic Nerve"; *J. Artif. Organs. (Jinkoh Sohki)*; vol. 22, No. 2, pp. 364-369; 1993.

Sunderland, S.; "A Classification of Peripheral Nerve Injuries Producing Loss of Function"; *Brain*; vol. 74, No. 4, pp. 491-516; 1951.

Wakabayashi, Y. et al.; "Regeneration of Motor Nerve"; *Inflammation and Immunity*; vol. 9, No. 3, pp. 271-277; 2001.

Itoh, S. et al.; "Regernation of Motion Nerve and Artificial Nerve"; *Modern Treatment*; vol. 31, No. 12, pp. 115-123; 1999.

Wakabayashi, Y. et al.; "Artificial Nerve for Regeneration of Motion Nerve"; *Clinical Neuroscience*; vol. 18, No. 11, pp. 1280-1283; 2000.

Archibald, S. J. et al.; "A Collagen-Based Nerve Guide Conduit for Peripheral Nerve Repair: An Electrophysiological Study of Nerve Regeneration in Rodents and Nonhuman Primates"; *The Journal of Comparative Neurology*; vol. 306, pp. 685-696; 1991.

Itoh, S. et al.; "Synthetic Collagen Fibers Coated with a Synthetic Peptide Containing the YIGSR Sequence of Laminin to Promote Peripheral Nerve Regeneration in vivo"; *Journal of Materials Science: Materials in Medicine*; vol. 10, pp. 129-134; 1999.

Tong, X. et al.; "Sciatic Nerve Regeneration Navigated by Laminin-Fibronectin Double Coated Biodegradable Collagen Grafts in Rats"; *Brain Research*, vol. 663, pp. 155-162; 1994.

Colin, W. et al.; "Nerve Regeneration Through Collagen Tubes"; *J. Dent. Res.*, vol. 63(7), pp. 987-993; 1984.

Itoh, S. et al.; "A Study on Induction ofNerve Regeneration Using Bioabsorbable Tubes"; *J. Jpn. Soc. Surg. Hand.*; vol. 17(4), pp. 371-375; 2000.

Suzuki, K. et al.; "Development of PGA-Collagen Channel for Peripheral Nerve Regeneration-Functional Evaluation"; *Jpn. J. Artif. Organs*; vol. 27(2), pp. 490-494; 1998.

Kiyotani, T. et al.; "Peripheral Nerve Regeneration in a PGA-Collagen Composite Tube"; *Jpn J. Artif. Organs*; vol. 25(2), pp. 476-480; 1996.

Shimada, H. et al.; "Induction of Peripheral Nerve Regeneration Using Laminin-Fibronectin Double Coated Collagen Fiber Grafts"; *Jpn. J. Artif. Organs*; vol. 22(2), pp. 359-363; 1993.

Kline, D. G. et al.; "The Use of a Resorbable Wrapper for Peripheral-Nerve Repair"; *Journal of Neurosurgery*; vol. 21(9), pp. 737-750; 1964.

* cited by examiner

NERVE REGENERATION-INDUCING TUBE COMPRISING

This application is a 371 of international application PCT/JP2003/017014, which claims priority based on Japanese patent application No. 2002-379796 filed Dec. 27, 2002, which is incorporated herein by reference.

TECHNICAL FIELD

The present invention relates to a nerve regeneration-inducing tube. More particularly, the present invention relates to an instrument for regenerating a human tissue or organ, for example, a nerve fiber or a micro blood vessel, which was cut due to lesion or injury.

BACKROUND ART

In a case where a human tissue or organ such as a nerve or tendon is injured owing to an accident, disaster, or disease and the injury cannot be cured by self-recovery of a patient, a disorder occurs in perception, sensation, mobility, or the like. For such a patient, with the development of a technology for connecting injured areas under a microscope in recent years, therapeutics such as surgical suturing for connecting cut portions or nerve autotransplantation, by which a nerve or tendon of a patient himself or herself biopsied from another part of the body is transplanted to recover the lost function, has been effective.

However, when the injured region is too large, restoration by the above-mentioned connection is impossible and it has been necessary to obtain a nerve from another location where a disorder, if any, could be believed to be less important than the disorder of the injured area of concern and transplant it to the injured area. In this case, although the disorder is less important than the disorder at the portion where injury first occurred, the nerve at another location that has received no injury and is healthy is biopsied, resulting in a disorder in perception, sensation, or mobility being generated at that location.

There may be mentioned one including, first, a biopsy of a sura nerve and then transplanting of the nerve to an injured location. In this case, the problem is that usually skin sensation, etc. of the area from ankle to instep is lost.

Accordingly, there has been a keen demand for a therapeutic method that enables restoration of an injured area without causing any impediment to another area (ankle, etc.).

Various studies have been made with a view to recovery of original functions by forming a footing for the proliferation of a nerve cell using an artificial instrument in an injured area to regenerate the nerve.

For example, attempts have been made to regenerate a nerve by using a tubular structure made of a bioabsorbable material which prevents foreign matter from remaining in the human body (refer to Suzuki et al., "Artificial Organ", 1998, 27, 2, p. 490-494).

Although some cell proliferation is observed at both ends of the cut nerve when only the tubular structure is used, recovery by re-grafting the cut nerve has been difficult. The reason for this is that when cells proliferate, generally they adhere to the footing of the tubular structure and proliferate in such a direction that they cover the cut portion but mere covering of the cut portion leaves a gap between the cut ends and the proliferation of cells is suspended before the cells completely fill the cut portion.

Then, various attempts have been made to regenerate a nerve by forming a footing for inducing the proliferation of a nerve cell inside the tubular structure made of a bioabsorbable material. For example, an attempt has been made in which a bundle of collagen fibers is inserted into the tubular structure and coated with fibronectin (FN) (refer to JP-A 5-237139, H. Shimada et al., "Artificial Organ", 1993, 22, 2, p. 359-363).

However, since the end portion of the tubular structure is sutured with the nerve, the end portion of the above nerve regeneration-inducing tube is easily ruptured at a sutured portion and the nerve regeneration-inducing tube may be eliminated from the nerve during treatment. Since the end portion of the nerve is merely sutured with the end portion of the inducing tube, the nerve may erroneously grow to the outside of the tubular structure from a gap in the sutured portion. A cell other than the nerve cell may enter the inside of the tubular structure to block the growth of the nerve cell.

Therefore, an attempt has been made to regenerate a nerve by using a nerve regeneration-inducing tube having a space part for accepting a nerve at both ends (refer to JP 237139 B).

However, in this case, after the nerve regeneration-inducing tube is cut according to the length of a nerve injured area, a fastening sleeve (short tubular structure) must be connected to both ends to form a space part for accepting a nerve.

DISCLOSURE OF THE INVENION

It is an object of the present invention to provide a nerve regeneration-inducing tube in which a nerve is inserted into a tubular structure and can be easily sutured and fixed without resort to any special instruments or operations, thereby allowing nerve cells to efficiently proliferate and grow in the correct direction.

The present invention has been made in view of the above object. It has been found that the above object can be attained by forming a definite space part at one end of a tubular structure (A) made of a biodegradable material or bioabsorbable material and including therein a sponge-like matrix (B) made of a biodegradable material or bioabsorbable material and/or a linear nerve-inducing channel (C) in a nerve regeneration-inducing tube which has the tubular structure (A). The present invention has been accomplished based on this finding.

That is, according to the present invention, there are provided:

(1) a nerve regeneration-inducing tube, including: a tubular structure (A) made of a biodegradable material or bioabsorbable material including therein a sponge-like matrix (B) made of a biodegradable material or bioabsorbable material and/or a linear nerve inducing channel (C); and a definite space part formed at one end of the tubular structure (A);

(2) the nerve regeneration-inducing tube according to (1), in which the length of the space part is about 1 to 20 mm;

(3) the nerve regeneration-inducing tube according to (1), in which the biodegradable material is a protein, a polypeptide, or a derivative thereof decomposed by a decomposing enzyme in a living organism, acid, or alkali;

(4) the nerve regeneration-inducing tube according to (1), in which the bioabsorbable material is a porous substance which allows the permeation of liquid and gas;

(5) the nerve regeneration-inducing tube according to (1), in which the bioabsorbable material is a protein, polypeptide, a derivative thereof, polysaccharide or a derivative thereof, polylactic acid, polyglycolic acid, a copolymer of glycolic acid and lactic acid, a copolymer of lactic acid and ε-aminocaproic acid, or aliphatic polyester;

(6) the nerve regeneration-inducing tube according to (1), in which the biodegradable material or bioabsorbable material is collagen;
(7) the nerve regeneration-inducing tube according to (1), in which the tubular structure (A) is made of a fibrous material;
(8) the nerve regeneration-inducing tube according to (7), in which the fibrous material is a short fiber, long fiber, filament, floc, textile fabric, or non-woven fabric;
(9) the nerve regeneration-inducing tube according to (1), in which the sponge-like matrix (B) is a collagen sponge;
(10) the nerve regeneration-inducing tube according to (1), in which the nerve-inducing channel (C) is formed by at least one fiber which is inserted into the tubular structure (A) in a longitudinal direction;
(11) the nerve regeneration-inducing tube according to (1), in which the nerve-inducing channel (C) is formed by at least one hollow fiber in the tubular structure (A) in the longitudinal direction;
(12) the nerve regeneration-inducing tube according to (1), in which the nerve-inducing channel (C) penetrates through the sponge-like matrix (B);
(13) the nerve regeneration-inducing tube according to (1), in which the nerve-inducing channel (C) is a fiber or hollow fiber; and
(14) a method of using the nerve regeneration-inducing tube according to (1), including: suturing the end of a central nerve inserted into the space part with the tubular structure (A); and suturing the end of a peripheral nerve with the end portion devoid of the space part of the tubular structure (A) by means of a bio suture.

BEST MODE FOR CARRYING OUT THE INVENTION

Figure 1:
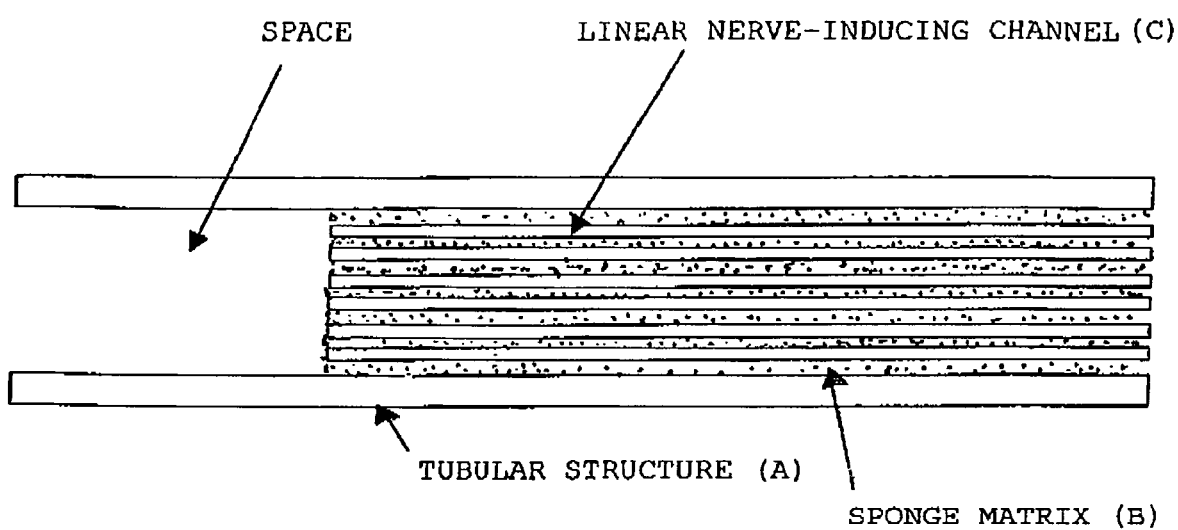
FIG. 1 is A sectional view in an axial direction of a nerve regeneration-inducing tube of the present invention.

The tubular structure (A) used in the present invention made of a biodegradable material or a bioabsorbable material is a tubular (hollow) mold, and its cross-sectional shape is not limited to a circular shape and may be selected from various shape such as an elliptical shape and a polygonal shapes depending on a nerve to be regenerated. However, the shape is preferably circular. The tubular structure (A) serves to secure a space part for nerve to regenerate from the infiltration of the surrounding tissue. The tubular structure (A) of the present invention is preferably, for example, a tubular structure constituted by a fibrous material made of a biodegradable material or bioabsorbable material. Examples of the fibrous material in this case include short fibers, long fibers, filaments, a floc, a textile fabric, and a non-woven fabric. The fiber diameter of the fibrous material is generally about 5 to 1,000 μm, and preferably about 10 to 100 μm. In particular, an inter-fiber interval of the support (A) is about 0 to 200 μm, preferably about 0 to 100 μm.

The outer diameter of the tubular structure (A) is generally about 0.1 to 50 mm, preferably about 0.5 to 25 mm. The inner diameter of the tubular structure (A) is generally about 0.05 to 40 mm, preferably about 0.3 to 20 mm.

Preferably, the tubular structure (A) includes a collagen sponge and a linear nerve-inducing channel (C) in its lumen portion.

In the present invention, one auxiliary means for regenerating nerve is a sponge-like matrix (B), which is constituted, for example, by a collagen sponge, a collagen fiber, or the like. The sponge-like matrix (B) gives suitable density and footing to cells in the nerve which is to be regenerated inside thereof. Also, short fibers, a floc, a non-woven fabric, and the like constituted by the collagen fiber are expected to have similar effects.

In the case where the sponge-like matrix (B) is a collagen sponge, the collagen sponge layer has a porosity of about 70 to 99.9%, and preferably about 80 to 99.9%. This collagen sponge may have at least one linear nerve-inducing channel (C) so as to penetrate therethrough in the longitudinal direction.

Furthermore, another auxiliary means is a linear nerve-inducing channel (C) which gives directivity of growth to a nerve cell being regenerated, to thereby reduce the time required for grafting the end of a central nerve to the end of a peripheral nerve. The nerve-inducing channel (C) is constituted by a large number of long fibers, filaments, a woven fabric, a knitted fabric, or a hollow fiber.

In the present invention, the definite space part formed at one end of the tubular structure (A) is a space part having a fixed length from the end portion in the lumen of the tubular structure (A) into which the matrix (B), the nerve-inducing channel (C), and other member are not inserted. Since most nerve cells grow only at the end of the central nerve, only the end of the central nerve has to be inserted into the tube, and an insertion portion does not need to be formed on both sides. The length (depth) of the space part is generally about 1 to 20 mm, preferably about 3 to 15 mm.

The biodegradable material used in the present invention is a material that is decomposed by a decomposing enzyme in a living organism, acid, or alkali, characterized by being porous to allow permeation of body fluid. Examples thereof include proteins such as collagen and gelatin, polypeptides, and derivatives thereof. Further, the bioabsorbable material is a porous substance which allows permeation of body fluid, for example, a protein or a polypeptide, or a derivative thereof, a polysaccharide or a derivative thereof, polylactic acid, polyglycolic acid, a copolymer of glycolic acid and lactic acid, a copolymer of lactic acid and ε-aminocaproic acid, or an aliphatic polyester such as a lactide polymer (see Patent Document 2). Of those, collagen is particularly preferable.

The origin of collagen used in the present invention is not limited and generally examples of its origin include cows, pigs, birds, fish, primate, rabbits, sheep, rats, and humans. The collagen can be obtained from skin, tendon, bone, cartilage, internal organs, or the like by various known extracting methods. However, the origin is not limited to those specific sites. Furthermore, the type of collagen used in the present invention is not limited to a particular classifiable type but in consideration of handling, types I, III, and IV are preferable. Production of the tubular structure (A) from those materials is performed according to a conventional method.

According to one embodiment of the present invention, there is provided a nerve regeneration-inducing tube having a collagen sponge with a porosity of about 70 to 99.9% and at least one linear space part formed in the longitudinal direction of the inside of a tubular structure (A) which has an outer diameter of about 0.5 to 20 mm and an inner diameter of about 0.3 to 15 mm and is constituted by a bundle of collagen fibers each having a fiber diameter of about 10 to 100 μm and penetrating through the sponge in the tubular structure (A).

According to another embodiment of the present invention, there is provided a nerve regeneration-inducing tube having a collagen sponge with a porosity of about 70 to 99.9% and a peripheral nerve regeneration-inducing channel or spinal nerve regeneration-inducing channel formed as a linear inducing channel (C) by inserting collagen fibers each having a diameter of about 5 to 1,000 µm in an amount equivalent to about 5 to 70% of the volume of the lumen portion or a hollow fiber having a diameter of about 5 to 1,000 µm in an amount equivalent to about 5 to 70% of the volume of the lumen portion in such a manner that it penetrates through the sponge layer in the tubular structure (A) which has an outer diameter of about 0.5 to 20 mm and an inner diameter of about 0.3 to 10 mm and is constituted by a bundle of collagen fibers each having a fiber diameter of about 10 to 100 µm.

The manufacturing method of the nerve regeneration-inducing tube of the present invention will herein after be explained in detail.

First, as an example of a manufacturing method for a tubular structure (A), a fibrous material, for example, short fibers, long fibers, filaments, a floc, a textile fabric, or a non-woven fabric is produced from a solution of a biodegradable material or a bioabsorbable material, for example, a collagen solution, according to a conventional method and then a tubular structure is produced from the material. The solvent for dissolving the collagen may be any known substance but use of water according to a conventional method is preferred. The concentration of the collagen solution is 0.1 to 30 wt %, preferably 0.5 to 10 wt %. The extrusion molding method for producing a collagen fiber is not particularly limited but usually a coagulating liquid is ethyl alcohol and an extrusion rate is about 100 to 500 mm/sec. Cooling of the fiber taken out from the coagulating liquid may be performed in the neighborhood of the degeneration temperature of collagen or lower, i.e. at about 40° C. or lower, but the temperature preferably is maintained at about 4 to 20° C. The diameter of the fiber is preferably about 10 to 100 µm.

To produce the tubular structure (A) from the fibrous material, for example, a continuous fiber produced by spinning of a collagen solution can be wound around a tubular substrate having a predetermined length to obtain a continuous fiber bundle having a uniform fiber direction. By removing the tubular substrate, the fiber bundle forms a hollow tubular structure. In the case where the tubular structure is used for restoring or regenerating a nerve such as a peripheral nerve or a spinal nerve, the tubular structure preferably has a suitable wall thickness of about 0.1 to 5 mm, an outer diameter of about 0.3 to 20 mm, an inner (lumen) diameter of about 0.1 to 10 mm, and any desired length. The diameter of the lumen portion depends on the diameter of the nerve to be grafted but in particular a range of from about 0.5 to 10 mm is suitable.

Thereafter, the auxiliary means for regenerating the nerve and a definite space part for accepting a nerve are provided in the lumen portion of the tubular structure (A).

The sponge-like matrix (B) filled in the lumen portion of the tubular structure (A) is formed by: injecting a collagen solution into the lumen portion of the support; and subjecting the resultant to natural drying, vacuum drying, or freeze vacuum drying. It is preferred that the sponge-like matrix (B) be formed uniformly by freeze vacuum drying in which the collagen solution is frozen after it is filled and dried in vacuum. The concentration of the collagen solution is about 0.05 to 30%. As for drying conditions, after the collagen solution is frozen, it is preferably kept at a vacuum degree of about 0.08 Torr or less.

The sponge-like matrix (B) means a state where there is formed a porous material having many domains with space parts of a uniform or non-uniform size dispersed continuously or discontinuously when visually judged or observed under a microscope. The matrix of a sponge layer formed in the lumen is produced by varying the concentration of the collagen solution used and filling a solution having a higher collagen concentration and a decreasing collagen concentration in sequence. By adjusting the concentration of the collagen solution to be filled, a matrix having layers with different space parts can be obtained and various forms of a matrix depending on the utility can be formed. When the ratio of the weight of the collagen filled in the lumen to the volume of the lumen of the tubular structure is expressed as a filling ratio, the filling ratio is preferably about 0.05 to 30% and, more preferably, the filling ratio is about 0.5 to 15%.

The nerve-inducing channel (C) is preferably formed such that it penetrates through the collagen sponge provided in the hollow portion of the tubular structure (A).

When the nerve-inducing channel (C) is constituted by collagen fibers, the diameter of each of the collagen fibers is generally about 5 to 1,000 µm, preferably about 10 to 100 µm. They are preferably inserted in an amount equivalent to about 5 to 70%, preferably about 10 to 60% of the inside volume of the above tubular structure (A).

When the nerve-inducing channel (C) is constituted by collagen fibers, the diameter of each of the collagen fibers is generally about 5 to 1,000 µm, preferably about 10 to 100 µm. They are preferably inserted in an amount equivalent to about 5 to 70%, preferably about 10 to 60% of the inside volume of the above tubular structure (A).

As an example of the manufacturing method when the nerve-inducing channel (C) is a hollow fiber, a tubular or columnar temporary substrate is inserted during the molding of the sponge-like matrix (B) and the temporary substrate is removed after molding to form a tubular gap as the nerve-inducing channel (C).

The sponge-like matrix (B) and the nerve-inducing channel (C) are made shorter than the length of the tubular structure (A). The sponge-like matrix (B) and/or the nerve-inducing channel (C) are/is arranged in the tubular structure (A) in contact with one end of the tubular structure (A). Thereby, a definite space part for accepting a nerve is formed at the other end.

The nerve regeneration-inducing tube obtained by the above method may be further subjected to any one of various known physical or chemical crosslinking treatments as required. The crosslinking treatment may be carried out in any stage. That is, the nerve regeneration-inducing tube may be composed of a tubular structure, matrix, nerve inducing channel, and the like which have been subjected to various crosslinking treatments, or the nerve regeneration-inducing tube may be formed and then subjected to any one of various crosslinking treatments. Two or more crosslinking treatments may be used in combination and the order thereof is arbitrary. This crosslinking treatment can drastically delay the degrading and absorbing time when the tube is transplanted into a living organism as compared with a case where no crosslinking treatment is carried out and improves physical strength. Therefore, when the injured area of the nerve is filled or sutured by the nerve regeneration-inducing tube, required strength can be maintained in the living organism during the time until the regeneration of a tissue is completed.

Examples of physical crosslinking include crosslinking treatments by γ-ray irradiation, UV irradiation, electron beam irradiation, plasma irradiation, and thermal dehydration reaction. Examples of the chemical crosslinking treatment include reactions with an aldehyde such as dialdehyde or polyaldehyde, epoxy, carboimide, or isocyanate, and a treatment with tannin or chromium.

The nerve regeneration-inducing tube obtained by the above method may be coated with a biodegradable substance. Examples of the biodegradable substance include collagen and hyaluronic acid.

Further, the proliferation ability of a cell can be activated by impregnating any one of growth factors, chemicals, and the like.

The nerve regeneration-inducing tube of the present invention is preferably sterilized by a known method such as γ-ray sterilization or ultraviolet radiation sterilization before it is used for a medical purpose. When collagen is used as a biodegradable material or bioabsorbable material, thermal sterilization is not preferred because the heat resistance of collagen is low.

The nerve regeneration-inducing tube of the present invention is sutured with a nerve tissue injured in vivo in accordance with a commonly used method and left until the nerve tissue is naturally cured in vivo. In the present invention, the nerve is the nerve tissue of a living organism, particularly preferably the peripheral nerve or spinal nerve of a human being.

Suturing means is an ordinary suture for a living organism and used to suture the end of the central nerve inserted into the space part with the tubular structure (A) of the inducing tube and the end of the peripheral nerve with the end portion devoid of the space part of the inducing tube. Since any inserted portion having a fixed length from the end portion of the tubular structure (A) of the end of the central nerve inserted into the space part may be sutured with the tubular structure (A), a suturing operation can be carried out easily as compared with the prior art. In the case of a cut nerve, the regeneration of the nerve can be seen simply by suturing the nerve regeneration-inducing tube with the end of the cut nerve.

The nerve-inducing tube obtained by the present invention has degradability and absorptivity in vivo and on the surface of a living organism which are inherent in collagen, is rarely toxic, and can be used safely for human beings and animals for medical purpose in accordance with a method known per se.

In the present invention, the nerve regeneration-inducing tube has been described. A similar tubular product can be used for other application purposes. For example, it can be transplanted in a living organism for filling and suturing in the tissue engineering and regeneration medical fields as, for example, an artificial windpipe, gullet, or ureter.

The following examples are provided for the purpose of further illustrating the present invention but are in no way to be taken as limiting.

EXAMPLE 1

Enzyme solubilizing collagen was first dissolved in water to prepare a 5% aqueous solution which was then extruded into a coagulating bath to manufacture a collagen fiber having a diameter of about 160 μm.

The obtained collagen fiber was wound round a cylindrical mold made of a polyethylene fluoride fiber having a diameter of about 2.5 mm. After the resultant was dried, it was impregnated with a 1% collagen aqueous solution and then with a 5% collagen aqueous solution to be coated while filaments wound round the cylindrical mold were dissolved. After the collagen fiber was wound, the resultant was impregnated with a collagen aqueous solution to form multiple layers so as to fabricate a collagen tubular structure. Further, a collagen fiber was wound round the outermost layer of the tubular structure. After the fiber was wound, the obtained tubular structure was subjected to a thermal crosslinking treatment. Thereafter, the thermally crosslinked cylindrical body was impregnated with a collagen aqueous solution and subjected to a thermal crosslinking treatment again. After the tubular structure was dried, it was thermally crosslinked to manufacture a collagen tubular structure 1 having an inner diameter of 2.5 mm, an outer diameter of 3.3 mm, and a length of 5 cm. A collagen fiber bundle 2 having a length of 4.5 cm was inserted into the lumen of the tubular structure 1 and a space part 3 having a length of 5 mm was formed at one end of the tubular structure 1 (see FIG. 1). A nerve regeneration-inducing tube essentially composed of collagen and having a structure that the lumen portion included a collagen fiber was manufactured.

EXPERIMENTAL EXAMPLE 1

Experiments on the regeneration of a nerve of a dog were carried out by using the nerve regeneration-inducing tube manufactured in Example 1. The peripheral nerve of the dog was selected as a tissue to be regenerated.

The nerve of the fibula of the dog was cut to prepare a 30 mm injured area. One end devoid of the space part of the nerve regeneration-inducing tube which was subjected to 25 kGy γ-radiation sterilization was cut to prepare a 35 mm tube piece in accordance with the length of the injured area. The length of the space part on a side opposite to the cut end was 5 mm. The central nerve of the fibula of the dog was inserted into the space part at one end of the tube and sutured with and fixed to the end of the tube by means of a 10-0 polyamide-based suture at a plurality of locations. The other end of the tube was sutured with and fixed to the cut end (peripheral side) of the nerve by means of a 10-0 polyamide-based suture at a plurality of locations.

Since the end portion of the central nerve was inserted into the space part of the nerve regeneration-inducing tube manufactured in Example 1 with certainty, suturing was able to be carried out easily. 30 days after suturing and fixing, the portion sutured with the nerve regeneration-inducing tube was taken out to confirm the state of nerve generation by hematoxylin-eosin (HE) dyeing. It was confirmed that the regeneration direction of the nerve was induced in the inducing tube without fail. An outside cell did not permeate from a gap in the sutured portion.

INDUSTRIAL APPLICABILITY

The end portion devoid of the space part of the nerve regeneration-inducing tube of the present invention can be cut according to the length of the injured area of the nerve during an operation to adjust its length easily due to its structure that the space part for accepting a nerve is formed only at one end.

A growth footing and directivity of growth are given to the regenerating cell, thereby making it possible to regenerate and restore a nerve injured area of interest quickly and surely.

Further, since the nerve regeneration-inducing tube has a definite space part at one end, the end portion of the nerve (central nerve) is inserted into the nerve regeneration-inducing tube surely and the regeneration direction of the nerve can be induced in the inducing tube surely. An outside cell does not permeate from a gap in the sutured portion.

Further, when the nerve regeneration-inducing tube of the present invention is used, any inserted portion having a fixed length from the end of the tubular structure (A) of the end of the central nerve inserted into the space part can be sutured with the tubular structure (A), a suturing operation can be easily performed and the nerve can be firmly sutured with the nerve regeneration-inducing tube as compared with the prior art.

The invention claimed is:

1. A method of using a nerve regeneration-inducing tube, the nerve regeneration-inducing tube comprising: a tubular structure (A) made of a biodegradable material or bioabsorbable material including therein a sponge matrix (B) made of a biodegradable material or bioabsorbable material and/or a linear nerve inducing channel (C); and an insertion space for insertion of a nerve end formed at only one end of the tubular structure (A);

the method comprising:

adjusting a length of the nerve regeneration-inducing tube by cutting the end of the nerve regeneration-inducing tube which devoid of the insertion space according to the length of the injured area of the nerve during an operation;

suturing an end of a central nerve inserted into the insertion space for insertion of a nerve end with the tubular structure (A); and suturing an end of peripheral nerve with the end portion devoid of the insertion space of the tubular structure (A) by means of a bio suture.

2. The method of using a nerve regeneration-inducing tube according to claim 1, wherein a length of the insertion space for insertion of a nerve end is about 1 to 20 mm.

3. The method of using a nerve regeneration-inducing tube according to claim 1, wherein the biodegradable material comprises a protein, a polypeptide, or a derivative thereof decomposed by a decomposing enzyme in a living organism, acid, or alkali.

4. The method of using a nerve regeneration-inducing tube according to claim 1, wherein the bioabsorbable material comprises a porous substance which allows permeation of liquid and gas.

5. The method of using a nerve regeneration-inducing tube according to claim 1, wherein the bioabsorbable material comprises a protein, polypeptide, a derivative thereof, polysaccharide or a derivative thereof, polylactic acid, polyglycolic acid, a copolymer of glycolic acid and lactic acid, a copolymer of lactic acid and $\epsilon$-aminocaproic acid, or aliphatic polyester.

6. The method of using a nerve regeneration-inducing tube according to claim 1, wherein the biodegradable material or bioabsorbable material comprises collagen.

7. The method of using a nerve regeneration-inducing tube according to claim 1, wherein the tubular structure (A) is made of a fibrous material.

8. The method of using a nerve regeneration-inducing tube according to claim 1, wherein the fibrous material comprises a short fiber, long fiber, filament, floc, textile fabric, or non-woven fabric.

9. The method of using a nerve regeneration-inducing tube according to claim 1, wherein the sponge matrix (B) comprises a collagen sponge.

10. The method of using a nerve regeneration-inducing tube according to claim 1, wherein the nerve-inducing channel (C) is formed by at least one fiber which is inserted into the tubular structure (A) in a longitudinal direction.

11. The method of using a nerve regeneration-inducing tube according to claim 1, wherein the nerve-inducing channel (C) is formed by at least one hollow fiber in the tubular structure (A) in the longitudinal direction.

12. The method of using a nerve regeneration-inducing tube according to claim 1, wherein the nerve-inducing channel (C) penetrates through the sponge matrix (B).

13. The method of using a nerve regeneration-inducing tube according to claim 1, wherein the nerve-inducing channel (C) comprises a fiber or hollow fiber.

* * * * *